United States Patent
Takahashi et al.

(10) Patent No.: US 6,558,317 B2
(45) Date of Patent: May 6, 2003

(54) AIR AND WATER SUPPLY SYSTEM FOR ENDOSCOPES

(75) Inventors: Kazuaki Takahashi, Omiya (JP); Haruo Akiba, Omiya (JP); Etsuko Sugikawa, Omiya (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 0 days.

(21) Appl. No.: 09/902,629

(22) Filed: Jul. 12, 2001

(65) Prior Publication Data

US 2001/0039370 A1 Nov. 8, 2001

Related U.S. Application Data

(62) Division of application No. 09/267,601, filed on Mar. 15, 1999, now Pat. No. 6,309,347.

(30) Foreign Application Priority Data

| Mar. 17, 1998 | (JP) | 10-89403 |
| Mar. 17, 1998 | (JP) | 10-89404 |
| Mar. 27, 1998 | (JP) | 10-100097 |
| Mar. 27, 1998 | (JP) | 10-100098 |
| Mar. 27, 1998 | (JP) | 10-100099 |

(51) Int. Cl.[7] ............................................. A61B 1/015

(52) U.S. Cl. ........................................ 600/158; 600/159

(58) Field of Search ................................. 600/156–159

(56) References Cited

U.S. PATENT DOCUMENTS 4,402,310 A * 9/1983 Kimura ........................ 600/158
5,343,855 A * 9/1994 Iida et al. ..................... 600/157

* cited by examiner

*Primary Examiner*—John Mulcahy
(74) *Attorney, Agent, or Firm*—Snider & Associates; Ronald R. Snider (57) ABSTRACT

The present invention provides a system for endoscopes which can supply air and water according to each application by regulating air and water flow rates independently. Although air and water may be supplied with one pump, the present invention controls air and water flow rates separately by using an air supply pump and water supply pump and by controlling a plurality of open-close valves installed, for example, on atmospheric escape pipes. The air channel and water channel are connected, for draining, by a first connecting pipe. If the air supply pump is used also for water supply and the water supply pump is used also for air supply, it is possible to supply air and water at a high flow rate fast enough even for high-speed water injection. If a fixed flow rate is used for a specified time at the start, specific operations can be simplified.

5 Claims, 11 Drawing Sheets

|  | (A) AIR SUPPLY High | (B) AIR SUPPLY Low | (C) WATER SUPPLY |
|---|---|---|---|
| $V_{11}$ | CLOSE | CLOSE | OPEN |
| $V_{12}$ | CLOSE | CLOSE | CLOSE |
| $V_{13}$ | OPEN | OPEN | CLOSE |
| $V_{14}$ | CLOSE | CLOSE | CLOSE |
| $V_{15}$ | CLOSE | OPEN | CLOSE |

|    | (A) POWER ON | (B) AIR SUPPLY High | (C) AIR SUPPLY Low | (D) WATER SUPPLY High | (E) WATER SUPPLY Low | (F) DRAINING OF WATER CHANNEL |
|----|---|---|---|---|---|---|
| V1 | CLOSE | CLOSE | CLOSE | OPEN | OPEN | CLOSE |
| V2 | OPEN | OPEN | OPEN | CLOSE | CLOSE | OPEN |
| V3 | OPEN | OPEN | OPEN | CLOSE | OPEN | OPEN |
| V4 | CLOSE | CLOSE | OPEN | OPEN | CLOSE | CLOSE |
| V5 | OPEN | CLOSE | OPEN | OPEN | OPEN | CLOSE |
| V6 | OPEN | CLOSE | CLOSE | OPEN | OPEN | CLOSE |
| V7 | CLOSE | CLOSE | CLOSE | CLOSE | CLOSE | OPEN |

| | (A) POWER ON | (B) AIR SUPPLY High | (C) AIR SUPPLY Low | (D) WATER SUPPLY High | (E) WATER SUPPLY Low | (F) HIGHSPEED WATER INJECTION | (G) DRAINING OF WATER CHANNEL |
|---|---|---|---|---|---|---|---|
| V21 | CLOSE | CLOSE | CLOSE | OPEN | OPEN | CLOSE | CLOSE |
| V22 | OPEN | OPEN | OPEN | CLOSE | CLOSE | CLOSE | OPEN |
| V23 | OPEN | OPEN | OPEN | CLOSE | OPEN | CLOSE | OPEN |
| V24 | CLOSE | OPEN | OPEN | OPEN | CLOSE | CLOSE | CLOSE |
| V25 | OPEN | CLOSE | OPEN | OPEN | OPEN | CLOSE | CLOSE |
| V26 | OPEN | CLOSE | CLOSE | CLOSE | CLOSE | CLOSE | CLOSE |
| V27 | CLOSE | CLOSE | CLOSE | CLOSE | CLOSE | CLOSE | OPEN |
| V28 | CLOSE | CLOSE | CLOSE | CLOSE | CLOSE | OPEN | CLOSE |
| V29 | CLOSE | CLOSE | CLOSE | CLOSE | CLOSE | OPEN | CLOSE |

FIG. 10

| | (B) | (C) | (D) | (E) | (F) |
|---|---|---|---|---|---|
| (A) | WATER SUPPLY | | AIR SUPPLY | | DRAINING OF WATER CHANNEL |
| POWER ON | High → Low | | Low → High | | |
| V1 | CLOSE | OPEN | CLOSE | CLOSE | CLOSE |
| V2 | OPEN | CLOSE | OPEN | OPEN | OPEN |
| V3 | OPEN | CLOSE → OPEN | OPEN | OPEN | OPEN |
| V4 | CLOSE | CLOSE | OPEN | OPEN | CLOSE |
| V5 | OPEN | OPEN | OPEN → CLOSE | CLOSE | CLOSE |
| V6 | OPEN | OPEN | CLOSE | CLOSE | CLOSE |
| V7 | CLOSE | CLOSE | CLOSE | CLOSE | OPEN |

(WHEN LOW IS SELECTED)(WHEN HIGH IS SELECTED)

AIR AND WATER SUPPLY SYSTEM FOR ENDOSCOPES

This application is a Division of application Ser. No. 09/267,601, filed on Mar. 15, 1999 (now U.S. Pat. No. 6,309,347 issued Oct. 30, 2001.

BACKGROUND OF THE INVENTION

This application claims the priority of Japanese Patent Application Nos. 10-89403 and 10-89404 filed on Mar. 17, 1998, Nos. 10-100097, 10-100098 and 10-100099 filed on Mar. 27, 1998 which are incorporated herein by reference.

1. Field of the Invention

The present invention relates to an air and water supply system for endoscopes, and more particularly, to an arrangement for flow control of air and water supply through air feed tubes and water feed tubes installed in endoscopes.

2. Description of the Prior Art

Endoscopes are conventionally provided with air feed tubes, water feed tubes, etc. through which air and water (liquid) are supplied to the tip of the endoscope to clean the viewing window (objective lens surfaces) at the tip or remove water-drops from it as well as to inflate a body cavity such as the stomach by the air sent into the body of the subject under observation. After use, endoscopes are cleaned and drained through the water feed tubes before storage.

Figure 12:
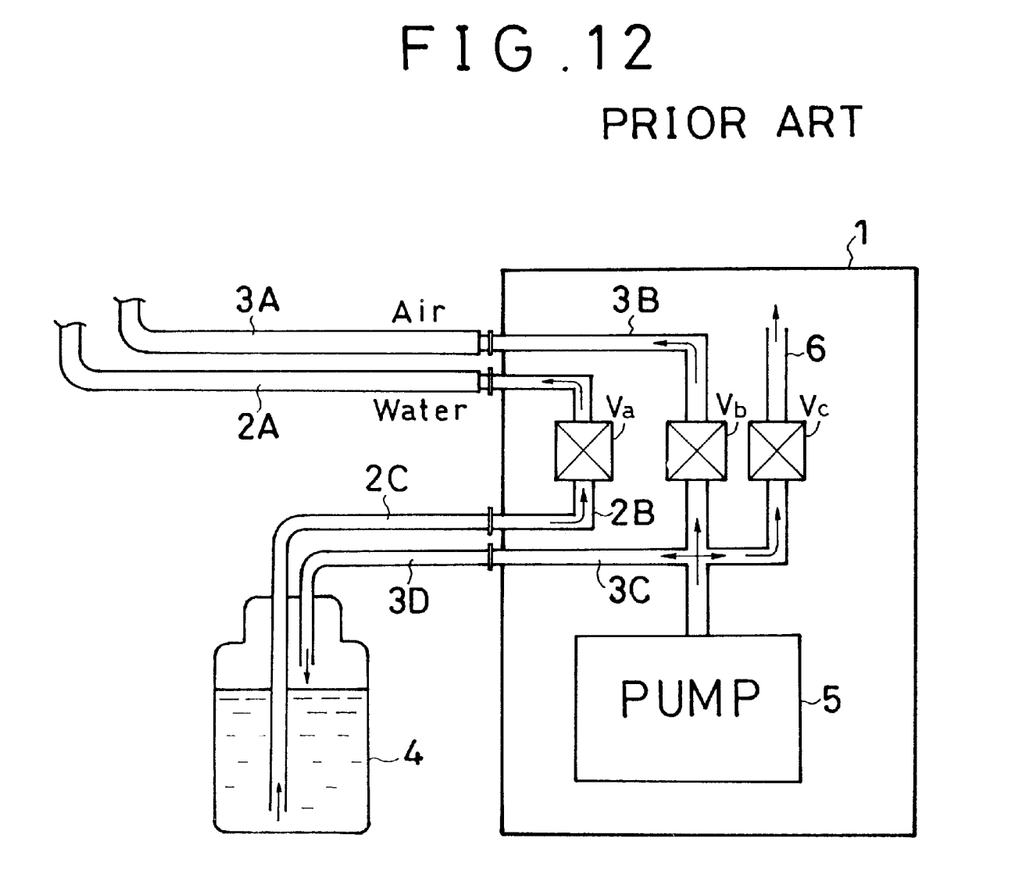
FIG. 12 is a diagram illustrating the configuration of a solenoid valve unit of a conventional endoscope.

FIG. 12 shows the configuration of a solenoid valve unit of a conventional endoscope. The water feed tube 2A and air feed tube 3A on the endoscope side are connected to the solenoid valve unit 1. The solenoid valve unit 1 comprises a water feed tube 2B, solenoid valve Va for controlling the opening and closing of the water feed tube 2B, air feed tube 3B, and solenoid valve Vb for controlling the opening and closing of the air feed tube 3B, wherein the water feed tube 2B is connected to a feed water tank 4 through a water feed tube 2C.

The solenoid valve unit 1 also contains an air and water supply pump 5, which is connected with the air feed tube 3B and a tube (air feed tube) for water supply 3C, which in turn is connected to the feed water tank 4 through a tube 3D. Furthermore the pump 5 is connected with an atmospheric escape pipe 6, which is equipped with a solenoid valve Vc. The control switch for air/water supply is installed, for example, on the operating section of the endoscope.

In the above configuration, when the air/water supply switch is not actuated, only the solenoid valve Vc remains open and the air sent from the pump 5 is released to the atmosphere through the atmospheric escape pipe 6. When the air/water supply switch is manipulated to supply water, the solenoid valve Va opens and the solenoid valves Vb and Vc close, allowing water to be supplied from the feed water tank 4 to the endoscope through the water feed tubes 2C, 2B, and 2A. When it is manipulated to supply air, the solenoid valve Vb opens and the solenoid valves Va and Vc close, allowing air to be supplied through the air feed tubes 3B and 3A.

BRIEF SUMMARY OF THE INVENTION

Object of the Invention

The conventional air and water supply systems of endoscopes are not able to regulate flow rates (quantities of flow per unit time): they control only the on/off operation of air/water supply. They are not capable of providing optimum air/water (liquid) supply individually according to application. Although the system in FIG. 12 described above is capable of adjusting the flow rates of air and water by changing the supply air pressure (capacity) of the pump 5 itself, it has a problem that is impossible to control air supply and water supply separately because changing the supply pressure of the pump 5 for air flow control will also change the flow rate of water.

For example, shooting out water at a relatively high flow rate (in the state of a large quantity of water per unit time) produces good results when cleaning the viewing window, whereas for subsequent drying, it is better to inject air at a relatively low flow rate, which will eliminate tiny droplets on the objective lens surfaces. Also, when inflating a body cavity such as the stomach (pneumoperitoneum) to apply an endoscope, it is necessary to feed air, taking into consideration the condition of the patient. Therefore, it is desirable if air and water can be supplied at a proper flow rate to suit the specific purposes of individual procedures. Besides, changing the supply pressure of the pump 5 in FIG. 12 between air supply and water supply may obstruct procedures because of time lags.

Furthermore, the endoscope is drained through the water feed tube 2A and air feed tube 3B after use, but there is a disadvantage that the supply air pressure during draining depends on the capacity of the pump 5, making optimum draining impossible.

Summary of the Invention

The present invention has been made in view of the above problems. The object of the present invention is to provide an air and water supply system for endoscopes that makes it possible to control air flow and water flow rates independently and supply air and water according to each application.

On the other hand, endoscopes have a flush water inlet port and an injection water inlet port installed on a operating section or the like. That is, the flush water inlet port is connected to the water channel of the endoscope. And water supplied through the flush water inlet port under high pressure with a syringe or the like can remove a high level of contamination from the objective lens surfaces of the viewing window. Also, an injection channel is installed in the endoscope to inject water to the object of observation. It is connected with the injection water inlet port installed on the operating section or the like. A liquid such as physiological saline is supplied through the injection water inlet port with a syringe or the like to remove foreign matters which would obstruct observation or treatment by adhering to objects under observation.

However, high-speed water injection and lens surface flushing, which are carried out by the use of accessories such as a syringe from the flush water inlet port and injection water inlet port installed on the operating section, involve complicated operations. Besides, injection with a syringe requires skill and experience of the physician. Moreover, these operations require a fast and ample flow of water, which conventional pumps cannot provide.

Another object of the present invention is to provide an air and water supply system for endoscopes that will allow high-speed water injection and lens surface flushing to be performed with simple switch operations.

Furthermore, the air and water supply system for endoscopes shown in FIG. 12 employ flexible tubing made of polyvinyl chloride (PVC) or the like for the water feed pipe 2A and air feed pipe 3A which connect the solenoid valve unit 1 with, for example, the light source fitted to the endoscope. And it has a problem that these flexible pipes (2A and 3A) may deform during air or water supply, changing the flow rate and failing to dry the lens surface of the viewing window sufficiently.

That is, the diameters of the water feed pipes 2 and the like used in the endoscope increase with approach to the solenoid valve unit 1, for example, the channel diameter inside the endoscope being approximately 1 mm, the tube diameter in the cable being approximately 2 mm, and the diameters of the above-mentioned flexible connecting pipes (2A and 3A) being approximately 5 mm. The walls of the flexible pipes are subject to some internal pressure. Thus the flexible pipes (2A and 3A) expand under this pressure during air or water supply, changing the flow rate at the start or end of air or water supply.

Furthermore, after supplying water to the lens surfaces to clean the viewing window, the pressure produced by the expanded connecting pipe 6C returning to the original shape will cause a small amount of water to leak from the nozzle at the distal end of the endoscope, resulting in poor water removal.

Still another object of the present invention is to provide an air and water supply system for endoscopes that can prevent changes in the flow rate and correct insufficient water removal by suppressing the expansion of the connecting pipes between the endoscope and channel control unit.

To attain the above objects, the present invention is characterized by comprising a pump for supplying air and water to the distal end through the air and water channels, a plurality of open-close valves installed on the air channel, water channel, and atmospheric escape channel connected to the pump, and a flow control section for specifying the air flow rate in the air channel and water flow rate in the water channel independently by controlling these valves. The flow control section allows the physician to vary the air flow rate while keeping the water flow rate constant.

According to the above described present invention, it is possible to set the air flow rate and water flow rate to different values, for example, by dividing the atmospheric escape pipe into a plurality of branch pipes and installing a solenoid valve in each of the branch pipes. For example, closing both solenoid valves installed in two atmospheric escape pipes will provide a High flow rate and closing only one of them will provide a Low flow rate. It is possible to switch the air flow rate between the High and Low setting while keeping the water flow rate at the High setting. This will make it possible to control both air and water flow rates through simple installation of solenoid valves in atmospheric escape pipes, eliminating the need to install separate means of control for air and water supplies, thus simplifying the configuration of the system.

Another aspect of the present invention is characterized by comprising an air channel, a water channel, an air supply pump, a water supply pump for supplying water independently of the air supply pump, and a controlling section for controlling the air supply pump and the water supply pump separately to regulate the air flow rate and water flow rate.

This aspect of the present invention comprises a first connecting pipe connecting the air channel and the water channel as well as an open-close valve for controlling the opening and closing of the first connecting pipe, of which the controlling section can supply air to at least the air channel.

It also comprises a second connecting pipe for connecting the water supply pump to the water channel to supply air as well as an open-close valve for controlling the opening and closing of the second connecting pipe, wherein the controlling section can use two pumps to supply air to the water channel.

According to the present invention, since independent air and water supply pumps are employed, their capacities can be selected separately to suit the purposes of air supply and water supply. The flow control means can also be employed separately for air supply and water supply. This makes it possible to specify the air flow rate and water flow rate per unit time individually according to application. The use of the first connecting pipe and its open-close valve allows air to be supplied to the water feed tube by the air supply pump at the optimum pressure for draining. Since two pumps can be used together, for example, to supply air to the water feed tube, and the intensity of air supply can be selected according to the condition of draining in this case.

Moreover, this aspect of the present invention can comprise a third connecting pipe for connecting the air supply pump to the water channel to supply water as well as an oepn-close valve for controlling the opening and closing of the third connecting pipe, wherein the controlling section can use two pumps to supply water to the water channel.

It also comprises an injection channel, apart from the water channel, for injecting water to objects under observation, the injection channel being connected to the third connecting pipe to allow water to be supplied to the injection channel with two pumps.

According to this aspect of the present invention, if the air supply pump is connected, for example, to the water feed tube through the third connecting pipe and its open-close valve, both air and water supply pumps can be used to secure the force and quantity of water supply necessary to flush the lens surfaces. Advantageously, the air supply pump can also be connected through a connecting pipe and open-close valve to the injection channel installed apart from the water channel, to secure the force and quantity of water supply necessary for high-speed water injection by using both air and water supply pumps.

Still another aspect of the present invention comprises a channel for supplying air and water to the distal end, flow control means for controlling the flow rates of the air and water supply through this channel variably, a control switch for selecting the flow rate to be controlled by the flow control means and for performing the air or water supply, and a control section which controls the flow control means so as to supply air or water at a predetermined fixed flow rate for a specified time after the air supply or water supply operation is started by the control switch and then enable any flow rate specified by the control switch.

According to this aspect of the present invention, the flow control means incorporating, for example, multiple pairs of an atmospheric escape pipe and its open-close valve allows air supply and water supply to be controlled in two steps High and Low—or any number of steps. Supposing that the High water flow setting and Low air flow setting are most desirable when cleaning the objective lens surfaces of the viewing window, the fixed flow rate of water supply is preset at High and that of air supply is preset at Low. Accordingly, when water supply is started, water is always supplied at the High flow rate for the first several seconds, and then it is supplied at the selected flow rate. On the other hand, when air supply is started, air is always supplied at the Low flow rate for the first several seconds, and then it is supplied at the selected flow rate. It is possible to limit the use of a fixed flow rate to either air supply or water supply.

Yet another aspect of the present invention is characterized in that the connecting pipe between the endoscope-side air or water feed tube and the corresponding tube on the side of the channel control unit is a flexible pipe, which is equal or superior to the air or water feed tubes inside the endoscope in terms of resistance to deformation caused by internal pressure.

This connecting pipe can be made by coating the outer surface of a soft tube with reinforcing material to protect the soft tube against deformation while maintaining its flexibility. Possible reinforcing materials include heat-shrinkable tubing, meshes, and adhesive coils. This aspect of the present invention can make the connecting pipe equal or superior to the air or water feed tubes inside the endoscope in terms of resistance to deformation, preventing expansion of the connecting pipe due to air or water pressure.

DETAILED DESCRIPTION OF THE PREFERRED EMBODIMENTS

First Embodiment

Figure 1:
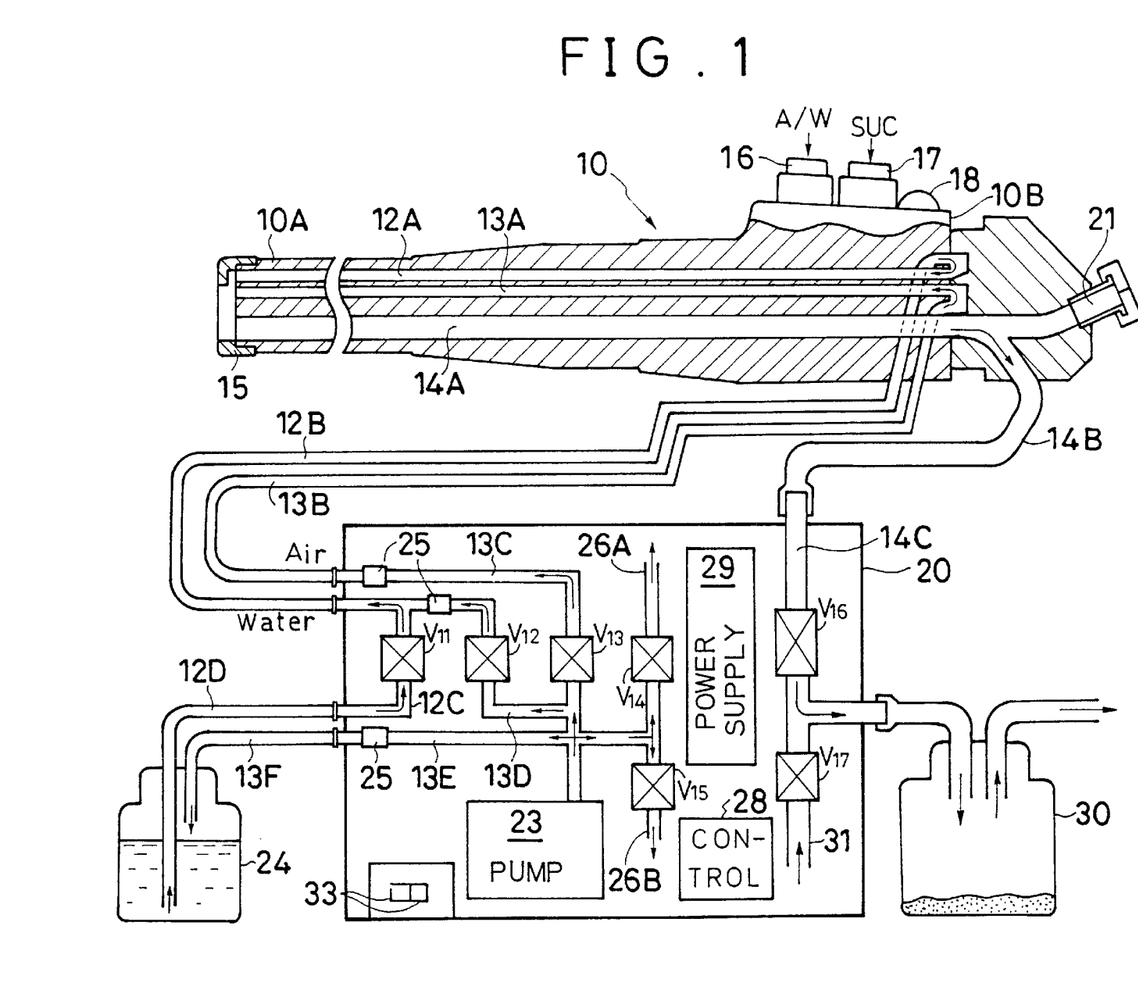
FIG. 1 is a diagram showing the overall configuration of an endoscope with the application of the air and water supply system according to the first embodiment of the present invention.

FIG. 1 shows the configuration of the air and water supply system for endoscopes according to the first embodiment of the present invention. As shown in the figure, the endoscope (electronic endoscope) 10 has a water feed tube 12A, an air feed tube 13A, and a suction tube 14A running from a distal end 10A to a operating section 10B. The tip of the distal end 10A is fitted with a detachable cap 15, on which a nozzle or the like are installed to supply air and water to the viewing window (lens surfaces of an objective optical system).

The operating section 10B contains an air/water supply switch 16, which is a two-step switch, a suction switch 17, and a picture button 18, as shown in FIG. 1. The operation control signals of the switches 16 and 17 are supplied to a solenoid valve unit 20. A water feed tube 12B and an air feed tube 13B are installed in a cable to connect the operating section 10B and the solenoid valve unit 20. A channel unit 10C is releasably attached to the backside of the operating section 10B. The folded portion formed when a channel unit 10C is attached connects the water feed tube 12A with the water feed tube 12B, and the air feed tube 13A with the air feed tube 13B.

The channel unit 10C is fitted with a suction tube 14B extending to the solenoid valve unit 20. A suction tube 14B bifurcates and one of the branches is fitted with a forceps inlet port 21.

The solenoid valve unit 20 contains a water feed tube 12C with a solenoid valve V11 (open-close valve), an air feed tube 13C with a solenoid valve V13, a pump 23, and an auxiliary air feed tube 13D with a solenoid valve V12 for supplying air from the pump 23 to the water feed tube 12B. The auxiliary air feed tube 13D and a solenoid valve V12 are used to drain the water feed tubes 12A and 12B on the endoscope side.

The water feed tube 12C is connected through a water feed tube 12D to a feed water tank 24, which is connected through a tube 13F with a tube (air feed tube) 13E, which in turn is connected to the pump 23. Each of the air feed tubes 13C, 13D, and 13E is provided with a check valve 25 to prevent water and the like from flowing backward into the air feed tubes (13C to 13E) in the solenoid valve unit 20, thus keeping their inside from being contaminated.

The pump 23 is connected with atmospheric escape pipes 26A and 26B which merge into one pipe before connecting to the pump 23 and which are equipped with solenoid valves V14 and V15. The solenoid valve unit 20 also contains a controlling section 28 for controlling the above-mentioned solenoid valves V11 to V15 (and to V17), a power supply unit 29, etc. The closing and opening of the solenoid valves V14 and V15 regulate the flow rates of air supply and water supply separately.

Since the supply air pressure of the pump 23 varies depending on whether one or both of the solenoid valves V14 and V15 are closed, the flow rates of air supply and water supply can be changed by changing the Open/Close pattern of the solenoid valves V14 and V15.

Furthermore, the solenoid valve unit 20 contains a suction tube 14C equipped with a solenoid valve V16 and connected to the suction tube 14B. The suction tube 14C is connected to a suction tank 30, which is also connected with a suction pump not shown in the figure. Also, the suction tube 14C is connected with an atmospheric escape pipe 31 and solenoid valve V17.

The control panel of the solenoid valve unit 20 is equipped with a flow control switch 33, which can be used to control the flow rate of air supply in two steps (High and Low). This flow control can also be performed with a control switch on the operating section 10B. For example, an air flow control switch may be provided separately from a water flow control switch as a two-step switch or as a control switch that allows stepwise control by sensing the pressing force of switch manipulation.

For example, this control switch will employ a pressure sensitive diode, piezo resistive micromachined silicon element, or the like as a pressure sensor, which will be pushed by an final control element (pushbutton) moved up and down (or a sensor which detects the length of an operating stroke). This arrangement will make it possible to regulate the air flow rate by controlling the opening and closing of the solenoid valves V14 and V15 according to the stepwise pressing force of the final control element.

This embodiment has the configuration just described, where the actuation of the solenoid valve unit 20 actuates the pump 23 and opens, for example, the solenoid valves V14 and V15 (or it is also possible to open only one of them), releasing the air in the pump 23 into the atmosphere (V17 is opened on the suction side). To supply air or water, the physician should operate the flow control switch 33 on the solenoid valve unit 20 and the air/water supply switch 16 on the operating section 10B of the endoscope. The Open/Close states of the solenoid valves V11 to V15 at this time are shown in FIG. 2.

Figure 2:
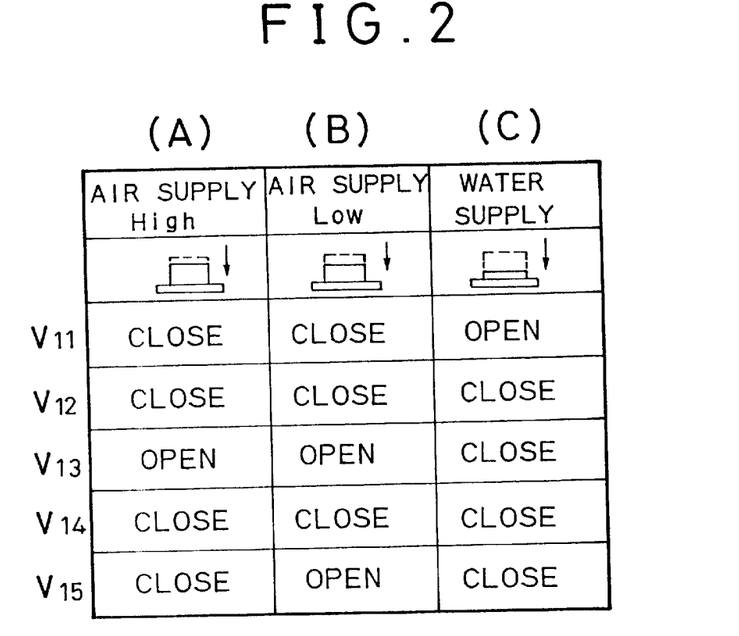
FIG. 2 is an explanatory drawing showing the relationship between air or water supply operations and solenoid valve operations according to the first embodiment of the present invention.

Specifically, pressing the first step of the air/water supply switch 16 with the flow control switch 33 set at High opens only the solenoid valve V13 and closes the other solenoid valves V11, V12, V14, and V15, as shown in FIG. 2, Column (A). Since both atmospheric escape pipes 26A and 26B are closed, air is supplied through the air feed tubes 13C to 13A at the higher flow rate. For example, air can be sent to a body cavity such as the stomach in a short time.

On the other hand, pressing the second step of the air/water supply switch 16 under the above-mentioned condition opens only the solenoid valve V11 and closes the other solenoid valves V12 to V15, as shown in FIG. 2, Column (C). Since both atmospheric escape pipes 26A and 26B are closed also in this case, water is supplied through the water feed tubes 12C to 12A at the higher flow rate. This mode can be used, for example, to remove contamination from the viewing window with good results by supplying water at a relatively high flow velocity.

Now, pressing the first step of the air/water supply switch 16 with the flow control switch 33 set at Low opens the solenoid valves V13 and V15 and closes the other solenoid valves V11, V12, and V14, as shown in FIG. 2, Column (B). Since only one atmospheric escape pipe 26A is closed, air is supplied at the lower flow rate. This mode can be used, for example, to dry the viewing window after the above-mentioned cleaning with good results by supplying air at a relatively low flow velocity.

When the suction switch 17 shown in FIG. 1 is pressed; the solenoid valve V16 opens and the solenoid valve V17 closes, suction is performed through the suction tubes 14C to 14A, and filth and the like are sucked through the distal end 10A and discharged to the suction tank 30.

With the present system, the water feed tubes 12A and 12B can be drained by the use of the air feed tube 13D and solenoid valve V12. Specifically, when only the solenoid valve V12 is opened and the other solenoid valves V11 and V13 to V15 are closed, air is sent from the pump 23 through the water feed tubes 12B and 12A to the distal end, draining the given channel. This draining operation is performed to clean the channel after using the endoscope.

In the above example, the flow rate of air supply was changed in two steps, but the flow rate may be changed in several steps for air supply and water supply separately.

As discussed above, the first embodiment allows air and water to be supplied at the flow rate suitable for a specific purpose. Besides, as flow control means, solenoid valves are installed in the atmospheric escape pipes connected to the pump to change the flow rate of the fluid coming out of the tubes concerned, eliminating the need to provide separate means for controlling air supply and water supply, and thus simplifying the configuration.

Second Embodiment

Figure 3:
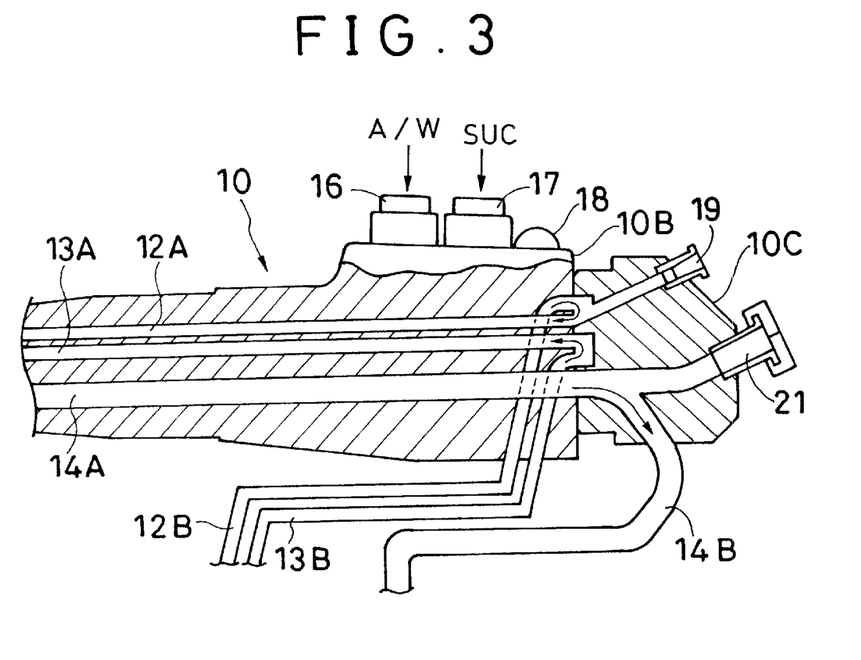
FIG. 3 is a drawing illustrating the configuration of the system on the endoscope side according to the second embodiment of the present invention.
Figure 4:
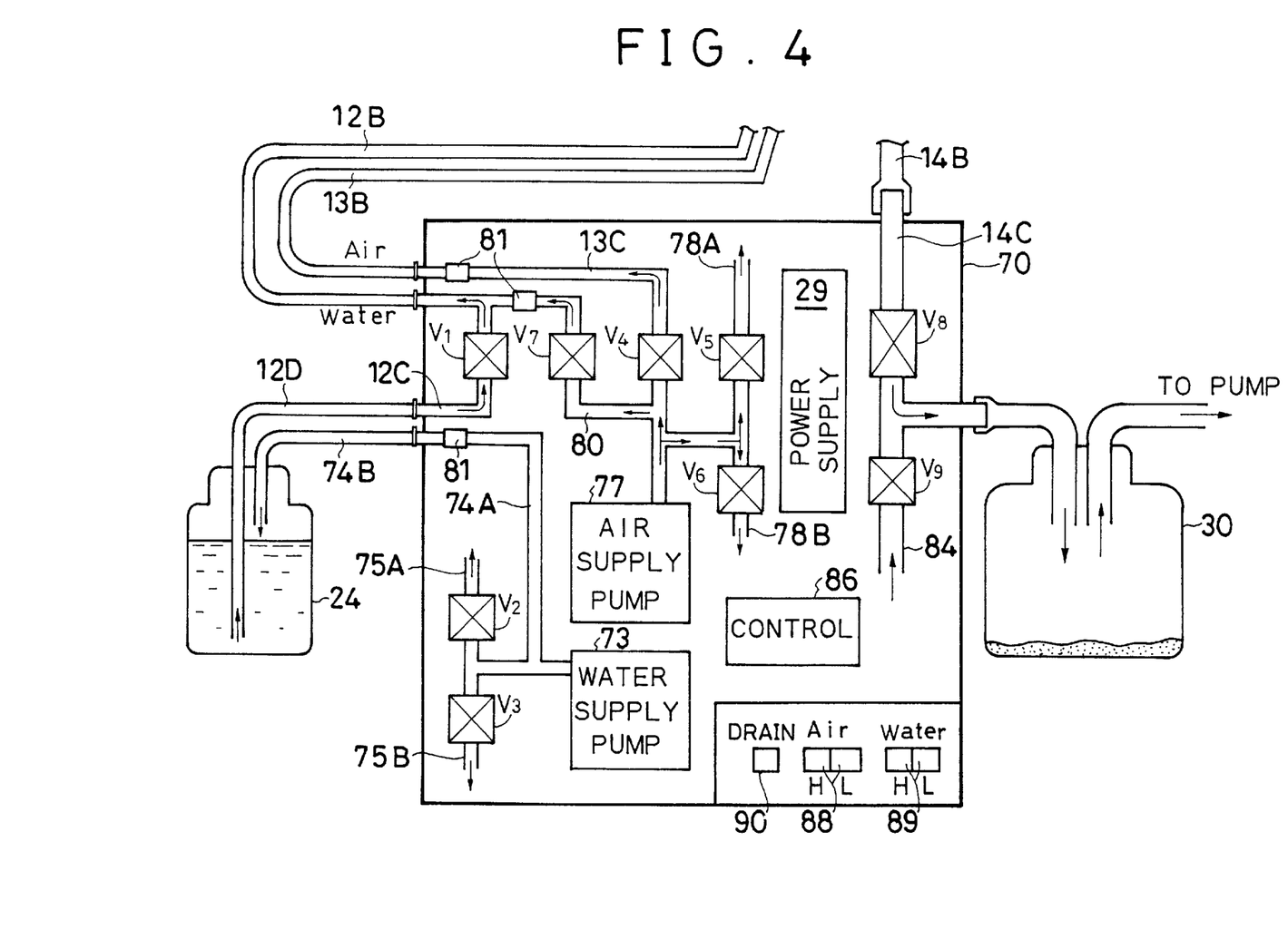
FIG. 4 is a diagram illustrating the configuration of the system on the solenoid unit side according to the second embodiment of the present invention.

FIG. 3 and FIG. 4 show the configuration of the air and water supply system for endoscopes according to the second embodiment of the present invention. The configuration on the endoscope side is almost the same as that shown in FIG. 1. As shown in FIG. 3, however, this embodiment has water feed tubes 12 equipped with a flush water inlet port 19, which is used to feed air/water by the use of a syringe or the like when the objective lens surfaces are heavily contaminated.

As shown in FIG. 4, the solenoid valve unit 70 contains a water feed tube 12C equipped with a solenoid valve V1 (open-close valve) and connected to the above-mentioned water feed tube 12B. The water feed tube 12C is connected to a feed water tank 24 through a water feed tube 12D. The solenoid valve unit 70 also contains a water supply pump 73, to which the feed water tank 24 is connected through tubes (air feed tubes) 24A and 24B. The water supply pump 73 is connected with atmospheric escape pipes 75A and 75B which merge into one pipe before connecting to the water supply pump 73 and which are equipped with solenoid valves V2 and V3, whose opening and closing actions control water supply in two steps (High and Low). That is, since the supply air pressure of the water supply pump 73 varies depending on whether one or both of the solenoid valves V2 and V3 are closed, the flow rate of air supply to the feed water tank 24 can be changed by selecting whether to close one or both of the solenoid valves.

On the other hand, an air feed tube 13C and solenoid valve V4 are connected between the endoscope-side air feed tube 13B and an air supply pump 77. In this embodiment, the air supply pump 77 has a capacity (air supply pressure) different from that of the water supply pump 73, but, of course, it may have the same capacity. The air supply pump 77 is also connected with atmospheric escape pipes 78A and 78B which merge into one pipe before connecting to the air supply pump 77 and which are equipped with solenoid valves V5 and V6, whose opening and closing actions can control air supply in two steps (High and Low).

A first connecting pipe 80 extends from the air feed tube 13C in the output section of the air supply pump 77 to the water feed tube 12C. It is fitted with a solenoid valve V7 and supplies the air for draining the water feed tubes 12B and 12A with the help of the solenoid valve V7. The air feed tubes, 13C, 74A, and 80 are all fitted with a respective check valve 81 to prevent water and the like from flowing backward into the air feed tubes 13C, 74A, and 80.

Furthermore, the solenoid valve unit 70 contains a suction tube 14C equipped with a solenoid valve V8 and connected to the suction tube 14B. The suction tube 14C is connected to a suction tank 30. Also, the suction tube 14C is connected with an atmospheric escape pipe 84 and solenoid valve V9. The opening and closing of the solenoid valves V1 to V9 are controlled form a controlling section 86.

The control panel of the solenoid valve unit 70 is equipped with flow control switches: an air flow control switch 88 for switching the air flow rate between High and Low, and a water flow control switch 89 for switching the water flow rate between High and Low, in this example. A drain switch 90 is also installed on the control panel.

This flow control can also be performed with a control switch on the operating section 10B described earlier. As described with respect to the first embodiment, a water flow control switch may be provided separately from an air flow control switch as a two-step switch or as a control switch that allows stepwise control using a pressure sensor by sensing the pressing force of switch manipulation. This arrangement will make it possible to regulate the air flow or water flow rate by controlling the opening and closing of the solenoid valves V2 and V3, or V5 and V6 according to the stepwise pressing force of the final control element.

Figure 5:
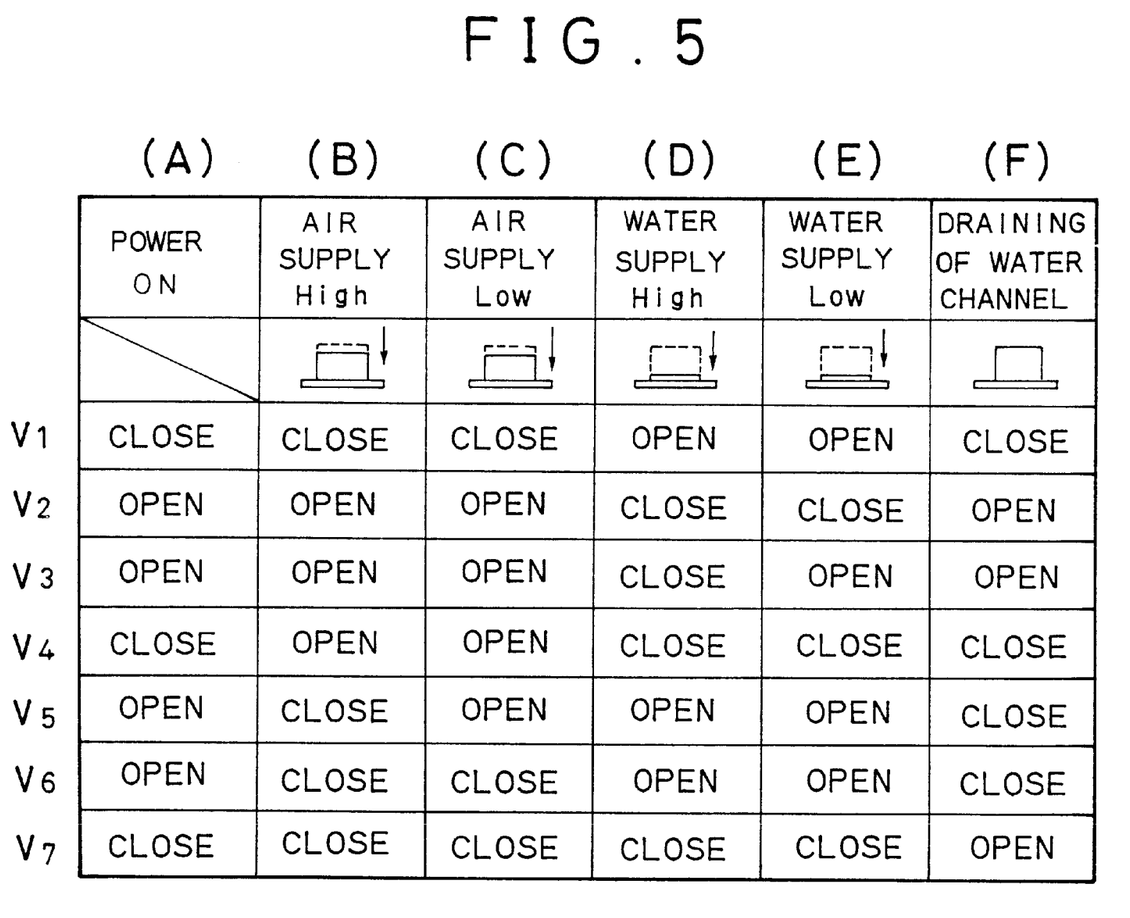
FIG. 5 is an explanatory drawing showing the relationship between air or water supply operations and solenoid valve operations according to the second embodiment of the present invention.

This embodiment has the configuration just described, where the air flow control switch 88 or water flow control switch 89, and the air/water supply switch 16 on the operating section 10B of the endoscope are manipulated for air or water supply. The Open/Close states of the solenoid valves V1 to V7 at this time are shown in FIG. 5. More precisely, the actuation of the solenoid valve unit 70 actuates the water supply pump 73 and air supply pump 77, opens the solenoid valves V2 and V3, for example, (or it is also possible to open only one of them), and opens the solenoid valves V5 and V6, as shown in FIG. 5, Column (A), releasing the air in the pumps 73 and 77 into the atmosphere (V9 is opened on the suction side).

Then, pressing the first step of the air/water supply switch 16 with the air flow control switch 88 set at High opens the solenoid valve V4 on the air feed tube 13C and closes the flow control solenoid valves V5 and V6, as shown in FIG. 5, Column (B). Since both atmospheric escape pipes 88A and 88B are closed, air is supplied through the air feed tubes 13C to 13A at the higher flow rate. For example, air can be sent to a body cavity such as the stomach in a short time.

On the other hand, pressing the second step of the air/water supply switch 16 with the water flow control switch 89 set at High opens the solenoid valve V1 on the water feed tube 12C and closes the flow control solenoid valves V2 and V3 as shown in FIG. 5, Column (D). Since both atmospheric escape pipes 75A and 75B are closed also in this case, water is supplied through the water feed tubes 12C to 12A at the higher flow rate. This mode can be used, for example, to remove contamination from the viewing window with good results by supplying water at a relatively high flow velocity.

Now, pressing the first step of the air/water supply switch 16 with the air flow control switch 88 set at Low opens the solenoid valve V4 on the air feed tube 13C and closes only the flow control solenoid valve V6 as shown in FIG. 5, Column (C). Since only one atmospheric escape pipe 78B is closed, air is supplied at the lower flow rate. This mode can be used, for example, to dry the viewing window after the above-mentioned cleaning with good results by supplying air at a relatively low flow rate.

On the other hand, pressing the second step of the air/water supply switch 16 with the water flow control switch 89 set at Low opens the solenoid valve V1 on the water feed tube 12C and closes only the flow control solenoid valve V2 as shown in FIG. 5, Column (E). Since only one atmospheric escape pipe 75A is closed also in this case, water is supplied at the lower flow rate.

Pressing the drain switch 90 of the solenoid valve unit 70 (for example, after using the endoscope) opens the solenoid valve V7 of the first connecting pipe 80 and closes the flow control solenoid valves V5 and V6 as shown in FIG. 5, Column (F). Consequently, air is sent from the air supply pump 77 through the water feed tubes 12C, 12B, and 12A to the distal end, draining and cleaning the given channel. In this way, air and water supply can be controlled separately at the flow rates suitable for a specific purpose.

When the suction switch 17 shown in FIG. 1 is pressed, the solenoid valve V8 opens and the solenoid valve V9 closes, suction is performed through the suction tubes 14C to 14A, and filth or the like is sucked through the distal end 10A and discharged to the suction tank 30.

Third Embodiment

Figure 6:
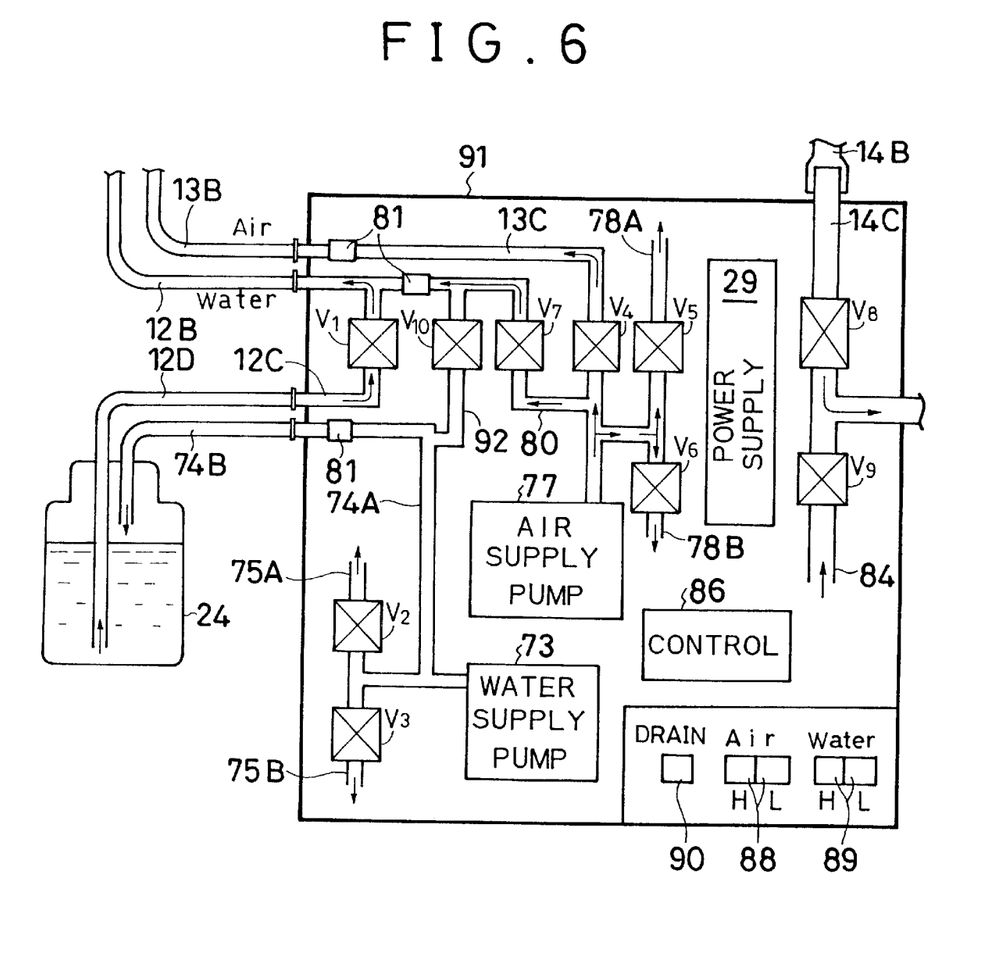
FIG. 6 is a diagram illustrating the configuration of the system on the solenoid valve unit side according to the third embodiment of the present invention.

FIG. 6 shows the configuration of the system according to the third embodiment of the present invention. This embodiment employs two pumps to drain the above-mentioned water feed tubes 12. It is almost the same as the second embodiment, but differs from it in that in a solenoid valve unit 91, a second connecting pipe 92 coming from the tube 74A connected to the water supply pump 73 is connected to the output side of the first connecting pipe 80 and fitted with a solenoid valve V10.

In this third embodiment, when a drain switch 90 of the solenoid valve unit 91 is pressed, a solenoid valve V7 of the first connecting pipe 80 and solenoid valve V10 of the second connecting pipe 92 are opened and flow control solenoid valves V5, V6, V2, and V3 are closed. Any of the solenoid valves V2, V3, V5, and V6 can be opened to reduce flow rates. This makes it possible to drain the water feed tubes 12C, 12B, and 12A by supplying air with both air supply pump 77 and water supply pump 73, allowing the tubes to be drained at a higher air flow rate than in the case of the second embodiment.

Although the above example explained only two-step flow control, any number of steps may be used actually. Also, although the first and second connecting pipes 80 and 92 were used to supply air to the water feed tubes 12, they can be configured to supply water to the air feed tubes 13.

As described above, the second and third embodiments broaden the choices of air flow rates by the use of the two pumps 73 and 77 and simplify the draining of water feed tubes by using the first and second connecting pipes 80 and 92.

Fourth Embodiment

Figure 7:
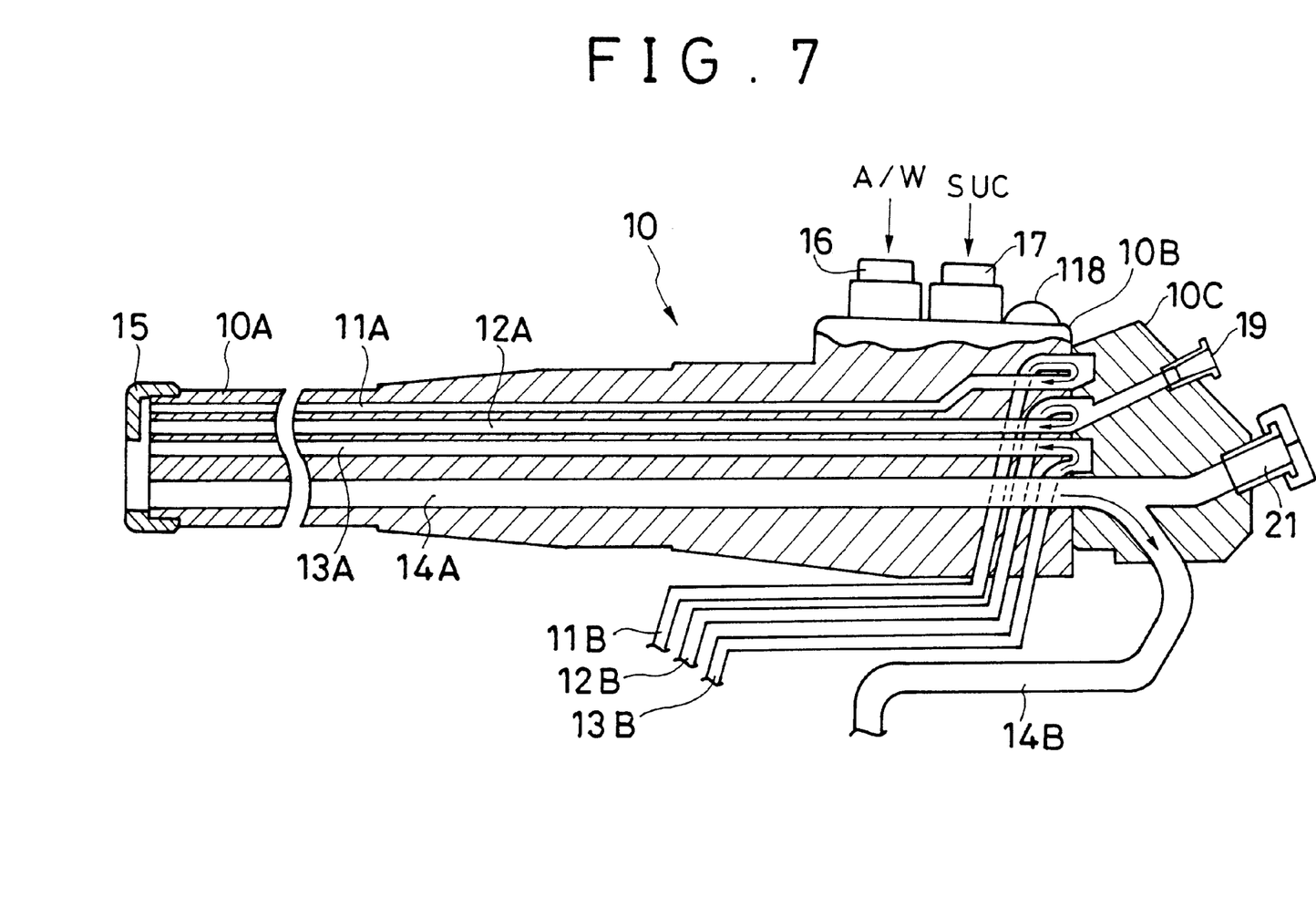
FIG. 7 is a drawing illustrating the configuration of the air and water supply system on the endoscope side according to the fourth embodiment of the present invention.
Figure 8:
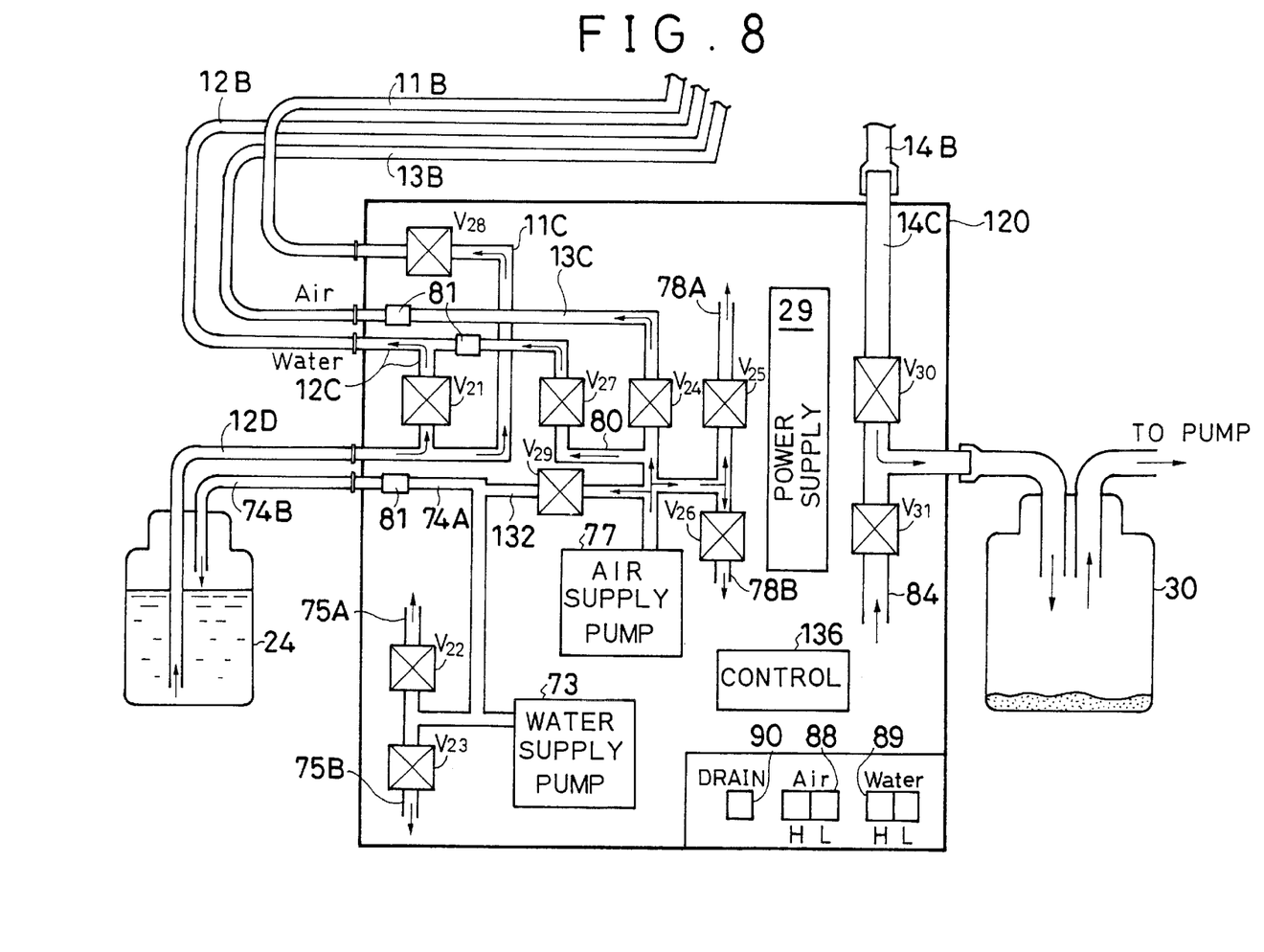
FIG. 8 is a diagram illustrating the configuration of the solenoid valve unit to be connected to the endoscope according to the fourth embodiment of the present invention.

FIGS. 7 and 8 show the configuration of the system according to the fourth embodiment of the present invention. As shown in FIG. 7, the endoscope 10 has injection pipes 11A and 11B running from the distal end 10A to the cable to inject water to objects under observation. Its operating section 10B is equipped with an injection switch 118. The rest of the configuration on the endoscope side is the same as the other embodiments described earlier. The operation control signals of the injection switch 118 are supplied to the solenoid valve unit 120 shown in FIG. 8.

As is the case with the solenoid valve unit in FIG. 4, the solenoid valve unit 120 in FIG. 8 contains a water feed tube 12C equipped with a solenoid valve V21 (which serves as an open-close valve), and atmospheric escape pipes 75A and 75B which merge into one pipe to connect to the air supply pump 73 and which are equipped with solenoid valves V22 and V23, whose opening and closing actions can control water supply in two steps (High and Low).

On the other hand, an air feed tube 13C equipped with a solenoid valve V24 is connected to an air supply pump 77, which may have a capacity (air supply pressure) different from or equal to that of the water supply pump 73 in this embodiment. The air supply pump 77 is also, as flow control means, connected with atmospheric escape pipes 78A and 78B which merge into one pipe before connecting to the air supply pump 77 and which are equipped with solenoid valves V25 and V26, whose opening and closing actions can control air supply in two steps (High and Low).

A first connecting pipe 80 extends from the air feed tube 13C in the output section of the air supply pump 77 to the water feed tube 12C. It is fitted with a solenoid valve V27 and supplies the air for draining the water feed tubes 12B and 12A with the help of the solenoid valve V27.

The injection pipe 11B in FIG. 7 is connected with an injection pipe 11C and a solenoid valve V28, then the injection pipe 11C is connected through the water feed tubes 12C and 12D to a feed water tank 24. Furthermore, a third connecting pipe 132 extends from the output section of the air supply pump 77 to a tube 74A on the side of the water supply pump 73. It is fitted with a solenoid valve V29 and they together make it possible to use the air supply pump 77 together with the water supply pump 73 for high-speed water injection or lens surface flushing.

Besides, the solenoid valve unit 120 has a suction tube 14C connected with a solenoid valve V30 and an atmospheric escape pipe 84 connected with a solenoid valve V31 and contains a controlling section 136 and the like for controlling the opening and closing of the solenoid valves V21 to V31. The air flow control switch 88 and the like on the control panel are the same as those for the second embodiment.

Figure 9:
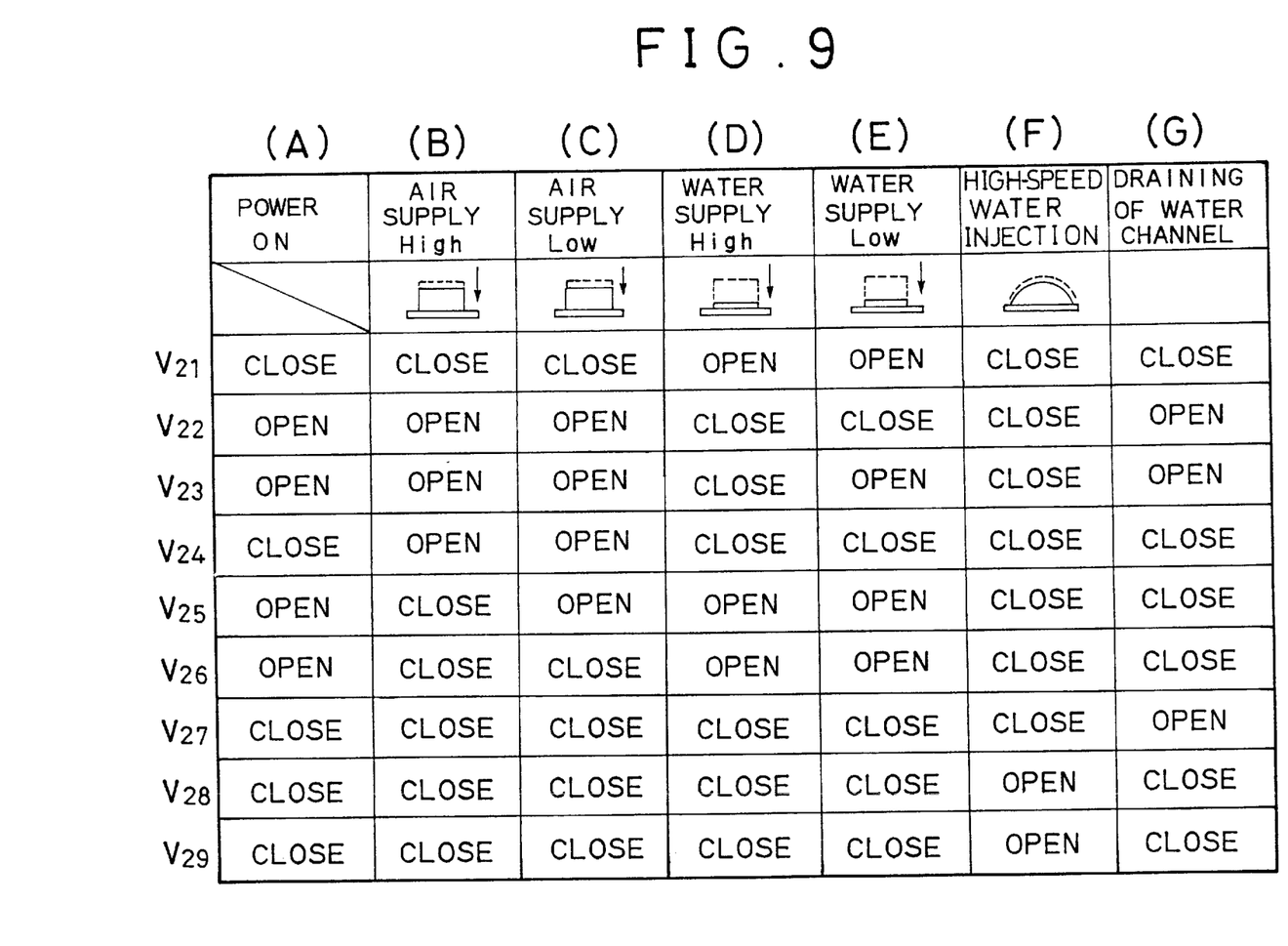
FIG. 9 is an explanatory drawing showing the relationship between air or water supply operations and solenoid valve operations according to the fourth embodiment of the present invention.

The fourth embodiment has the configuration just described and the Open/Close states of the solenoid valves V21 to V29 are shown in FIG. 9. The actuation of the solenoid valve unit 120 actuates the water supply pump 73 and air supply pump 77, opens the solenoid valves V22 and V23, for example, and opens the solenoid valves V25 and V26, as shown in FIG. 9, Column (A), releasing the air in the pumps 73 and 77 into the atmosphere.

Then, pressing the first step of the air/water supply switch 16 with the air flow control switch 88 set at High opens the solenoid valve V24 on the air feed tube 13C and closes the flow control solenoid valves V25 and V26, as shown in FIG. 9, Column (B). Since both atmospheric escape pipes 88A and 88B are closed consequently, pneumoperitoneum can be performed at a high flow rate in a short time.

On the other hand, pressing the second step of the air/water supply switch 16 with the water flow control switch 89 set at High opens the solenoid valve V21 on the water feed tube 12C and closes the flow control solenoid valves V22 and V23 as shown in FIG. 9, Column (D). Since both atmospheric escape pipes 75A and 75B are closed also in this case, cleaning of the viewing window and the like can be performed at a high flow rate.

Now, pressing the first step of the air/water supply switch 16 with the air flow control switch 88 set at Low opens the solenoid valve V24 on the air feed tube 13C and closes only the flow control solenoid valve V26 as shown in FIG. 9, Column (C). Since only one atmospheric escape pipe 88B is closed consequently, the viewing window can be dried after cleaning at a low flow rate.

On the other hand, pressing the second step of the air/water supply switch 16 with the water flow control switch 89 set at Low opens the solenoid valve V21 on the water feed tube 12C and closes only the flow control solenoid valve V22 as shown in FIG. 9, Column (E). Thus, water is supplied at the lower flow rate.

Pressing the injection switch 118 on the operating section 10B opens the solenoid valve V28 of the injection pipe 11C and the solenoid valve V29 of the third connecting pipe 132 while closing the flow control solenoid valves V29, V23, V25, and V26, as shown in FIG. 9, Column (F). Since water is supplied from the feed water tank 24 not only by the water supply pump 73, but also by the air supply pump 77, deposits and the like can be removed from the viewing window by very powerful water injection through the injection pipes 11B and 11A.

In this example, water is injected automatically at the maximum flow rate, but the system may be configured to regulate this flow rate with a separate switch, the air flow control switch 88, or the water flow control switch 89. For example, if the flow control switches 88 and 89 are used, the injection force and water quantity can be varied depending on whether one or both of the switches are set to Low.

Pressing the drain switch 40 of the solenoid valve unit 120 (for example, after using the endoscope) opens the solenoid valve V27 of the first connecting pipe 80 and closes the flow control solenoid valves V25 and V26 (V22 and V23 are open) as shown in FIG. 9, Column (G). Consequently, air is sent from the air supply pump 77 through the water feed tubes 12C, 12B, and 12A to the distal end, draining and cleaning the given channel. In this way, air and water supply can be controlled separately, using the flow rates suitable for a specific purpose.

This embodiment can also use the two pumps 73 and 77 to feed water and flush the lens surfaces. Specifically, a flush switch can be installed at any desired place and then this flush switch and the controlling section 136 can be manipulated to open the solenoid valve V21 on the water feed tube 12C and solenoid valve V29 on the third connecting pipe 132 and close the flow control solenoid valves V22, V23, V25, and V26, allowing the two pumps 73 and 77 to feed water at a high flow velocity through the water feed tubes 12B and 12A. This will make it possible to remove a large amount of stubborn dirt from the objective lens surfaces of the viewing window.

As described above, the fourth embodiment allows high-speed water injection and lens surface flushing to be performed with simple switch operation while providing the necessary injection force and water quantity.

Fifth Embodiment

The configuration of the fifth embodiment is the same as that of the second embodiment shown in FIGS. 3 and 4 except that the controlling section (86) installed in the solenoid valve unit 70 performs control actions different from those of the second embodiment. More particularly, the controlling section (86) enables the flow rates selected by the air flow control switch 88 and water flow control switch 89, but it uses a predetermined fixed flow rate for a specified time at the start when the air/water supply switch 16 is pressed and operated.

This embodiment fixes the water flow rate at High and the air flow rate at Low (the fixed flow rates are specified as required according to the supply air pressures of the pumps 73 and 77 as well as the number of control steps) to suit the air supply or water supply for cleaning of the viewing window and uses these flow rates for the first few seconds (2 to 5 seconds), and then switches to the flow rates selected by the flow control switches 88 and 89. This embodiment will be useful in situations, such as air supply for cleaning of the viewing window, where operation at fixed flow rates are desirable because it will be troublesome to adjust flow rates if the air or water flow rate can be selected freely.

Figure 10:
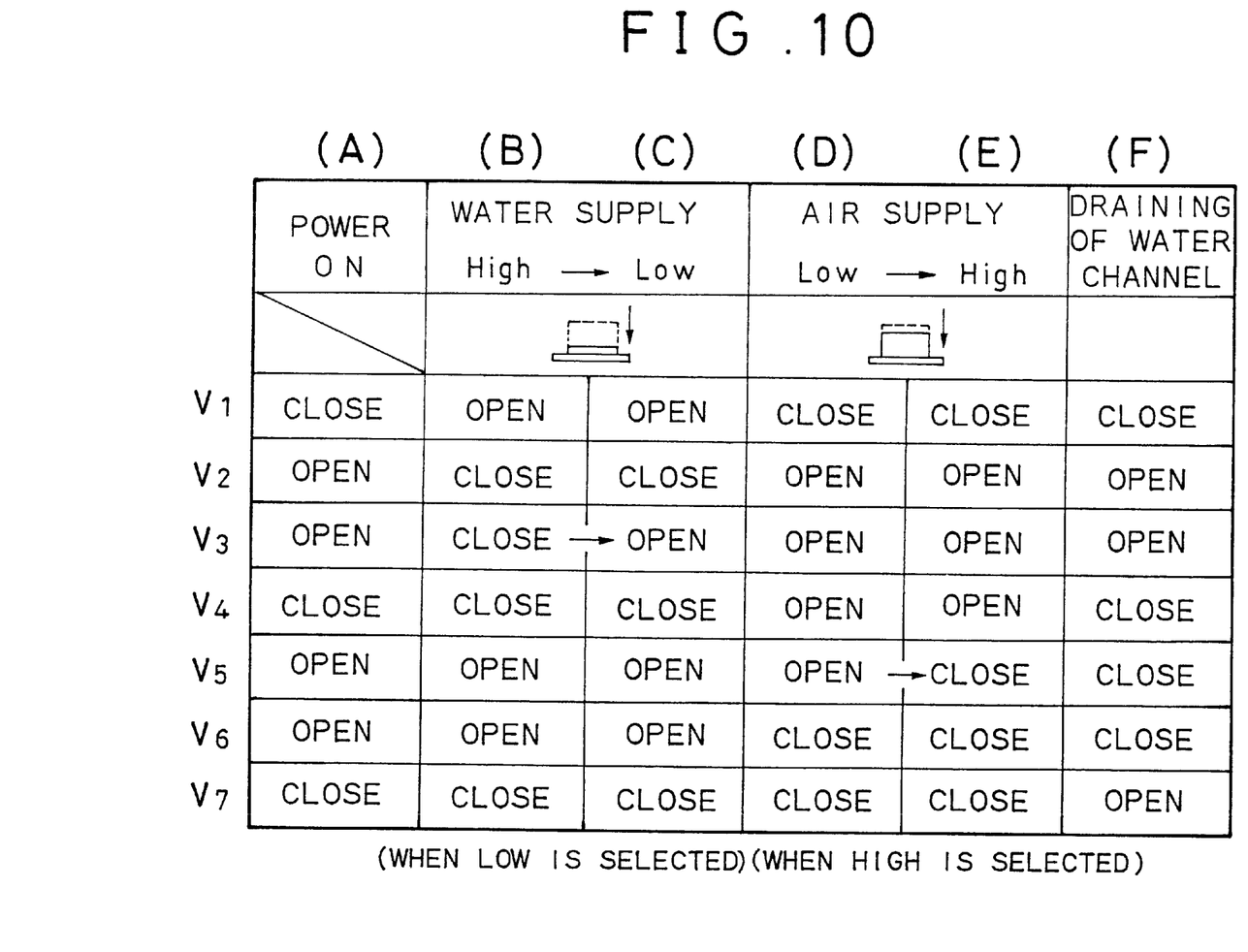
FIG. 10 is an explanatory drawing showing the relationship between air or water supply operations and solenoid valve operations according to the fifth embodiment of the present invention.

FIG. 10 shows the operation of the solenoid valves in the fifth embodiment. Pressing the second step of the air/water supply switch 16 with the water flow control switch 89 in FIG. 4 set at Low opens the solenoid valve V1 on the water feed tube 12C and closes the flow control solenoid valves V2 and V3 for the first few seconds, as shown in FIG. 10, Column (B). Both atmospheric escape pipes 75A and 75B of the water supply pump 73 are closed to supply water through the water feed tubes 12C to 12A at the higher flow rate for the first few seconds. Thus, contamination can be removed fairly well from the viewing window by water supplied at a relatively high flow velocity. Then, as shown in FIG. 10, Column (C), the flow control solenoid valve V3 opens (the other solenoid valves remain as they are), leaving only one 75A of the atmospheric escape pipes closed. Thus, water is supplied at the lower flow rate.

Then, pressing the first step of the air/water supply switch 16 with the air flow control switch 88 set at High opens the solenoid valve V4 on the air feed tube 13C (V2, V3, and V5 remain open) and closes only one flow control solenoid valve V6 (V1 remains closed) for the first few seconds, as shown in FIG. 10, Column (D). Consequently, only one atmospheric escape pipes 78B of the air supply pump 77 are closed to supply air through the air feed tubes 13C to 13A at the lower flow rate. This mode can be used to dry the viewing window after the above-mentioned cleaning with good results by supplying air at a relatively low flow rate.

Subsequently, as shown in FIG. 10, Column (E), the flow control solenoid valve V5 as well as both atmospheric escape pipes 78A and 78B are closed to supply air at the selected High flow rate. This mode allows air to be sent to a body cavity such as the stomach in a short time. Thus, when performing pneumoperitoneum, air is sent first at the optimum flow rate for drying and then at the optimum flow rate for pneumoperitoneum. When only drying the objective lens surfaces, what is needed is to cancel the setting of the air/water supply switch 16 in a few seconds and there is no need to select a flow rate setting.

Thus, advantageously, this embodiment simplifies the cleaning of the viewing window: even if a different flow rate has been selected for air or water supply, air or water is always fed at the optimum flow rate during cleaning of the viewing window, which is a frequently-performed operation.

Although in the above example, the fixed initial flow rate was set at High for water supply and at Low for air supply, it can be specified freely taking various conditions into consideration. It may be set at Low for water supply and at High for air supply, conversely. Or the specification of initial flow rate can be limited only to air supply.

As described above, according to the fifth embodiment, in variable control of air or water supply which involves air or water supply for cleaning of the viewing window, air or water is fed automatically at a predetermined flow rate, eliminating the trouble of regulating the flow rate.

Sixth Embodiment

Figure 11:
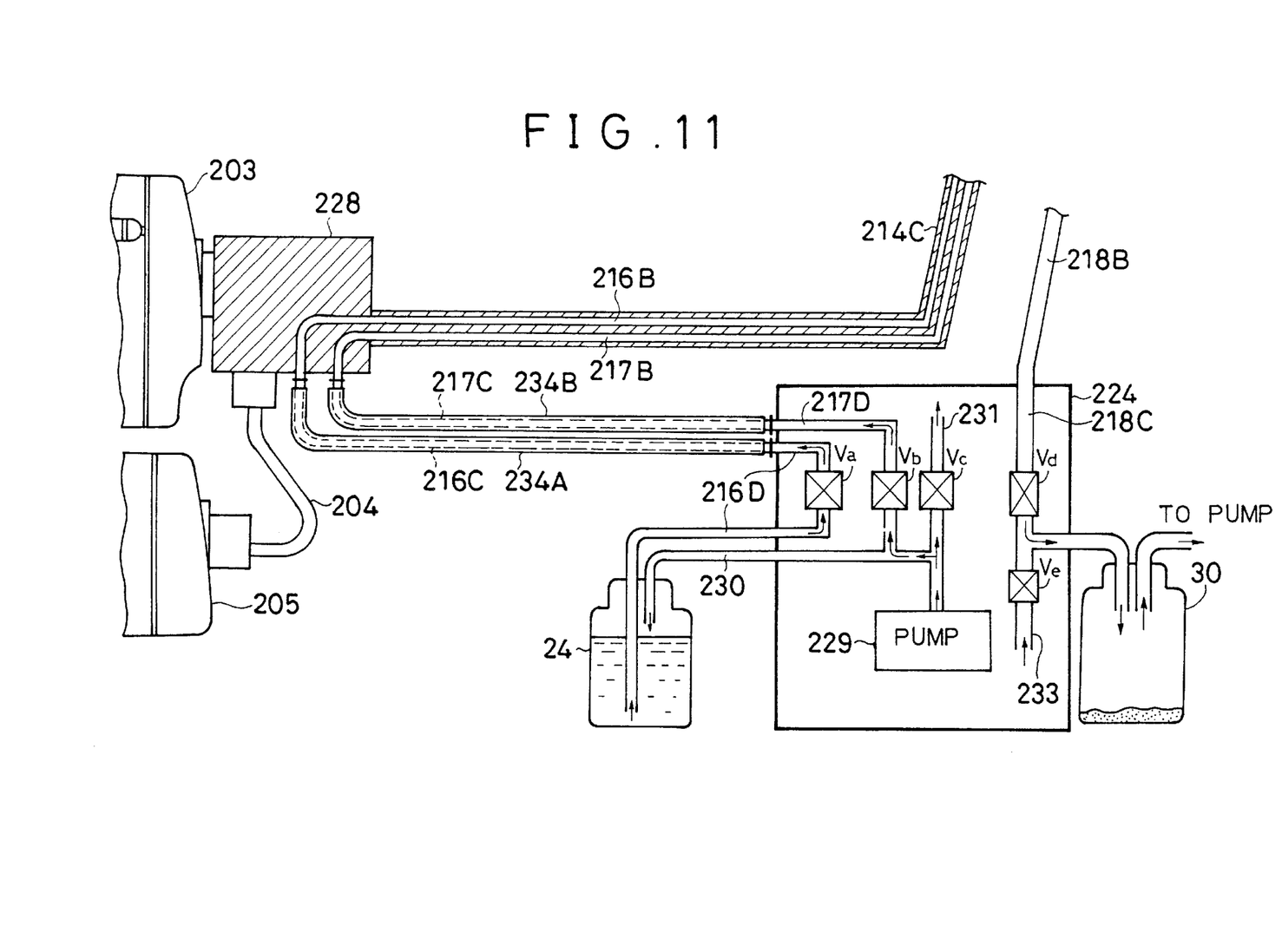
FIG. 11 is a diagram illustrating the configuration of the solenoid valve unit to be connected to the endoscope according to the sixth embodiment of the present invention.

FIG. 11 shows the configuration of the air and water supply system for endoscopes according to the sixth embodiment of the present invention. The cable 214C in FIG. 11 is identical to the cables used in the endoscopes according to the other embodiments. It is connected through a connector block 228 to a light source unit 203. Then it connects a light guide (not shown) to the light source in the light source unit 203. The cable 214C contains a water feed tube 216B and air feed tube 217B. These tubes are made of polytetrafluoroethylene (known as the trade name Teflon), etc. such that they will not expand under water or air pressure.

A signal wire contained in the cable 214C is connected to a processor unit 205 through a signal cable 204 branching off from the connector block 228. The connector block 228 is connected with a solenoid valve unit 224 through a water supply connecting pipe 216C and air supply connecting pipe 217C made of soft tubes (polyvinyl chloride or the like).

The solenoid valve unit 224 contains a water feed tube 216D equipped with a solenoid valve Va and connected to the connecting pipe 216C. The other end of the water feed tube 216D is connected to a feed water tank 24. The solenoid valve unit 224 also contains a pump 229, which is connected to the feed water tank 24 through a tube 230. On the other hand, the connecting pipe 217C is connected to an air feed tube 217D equipped with a solenoid valve Vb. The other end of the air feed tube 217D is connected to the pump 229, which is also connected with an atmospheric escape pipe 231 equipped with a solenoid valve Vc.

Furthermore, the solenoid valve unit 224 contains a suction tube 218C equipped with a solenoid valve Vd and connected to a suction tube 218B. The suction tube 218C is also connected with an atmospheric escape pipe 233 and a solenoid valve Ve.

The water supply connecting pipe 216C and air supply connecting pipe 217C are coated with reinforcing material, heat-shrinkable tubes 234A and 234B, which, after being fitted over the connecting pipes 216C and 217C, respectively, are heated to enhance adhesion to the outer surfaces of the connecting pipes while maintaining flexibility. After coating, the tubes 234A and 234B can suppress expansion of the soft (PVC) connecting pipes 216C and 217C.

Adhesive coils may be used instead of the heat-shrinkable tubes 234A and 234B to coat the connecting pipes 216C and 217C. Or the connecting pipes 216C and 217C themselves may be formed into wire-reinforced flexible tubes. The use of reinforcing material can protect the connecting pipes 216C and 217C from deformation or expansion under air or water pressure.

It is also possible to make connecting pipes 216C and 217C of polytetrafluoroethylene (fluororesin) as is the case with endoscope-side water feed tubes 216 A and 216B and air feed tubes 217 A and 217B, and set their wall thickness properly in order to make the deformation due to internal pressure approximately equal to that of the tubes 216A, 216B, 217A, and 217B.

The sixth embodiment has the configuration just described above, where the solenoid valve unit 224 performs air supply and water supply in a similar fashion to the system shown in FIG. 12. In doing that, the connecting pipe 216C is subjected to a certain water pressure, and the connecting pipe 217C to a certain air pressure. However, the heat-shrinkable tubes 234A and 234B suppress expansion of the connecting pipes 216C and 217C. Therefore, the air flow rate and water flow rate remain stable and the objective lens surfaces of the viewing window are dried properly after cleaning.

What is claimed is:

1. The air and water supply system for endoscopes comprising:
    an air channel for supplying air to the distal end of the endoscope;
    a water channel for supplying water to said distal end of the endoscope;
    an air supply pump for performing said air supply;
    a water supply pump for performing said water supply independently from said air supply pump; and
    a control section for controlling air flow and water flow rates individually by controlling said air supply pump and said water supply pump;
    a first connecting pipe for connecting said air channel and said water channel; and
    an open-close valve for opening and closing said first connecting pipe,
    wherein said control section supplies air to said water channel.

2. The air and water supply system for endoscopes comprising:
    an air channel for supplying air to the distal end of the endoscope;
    a water channel for supplying water to said distal end of the endoscope;
    an air supply pump for performing said air supply;
    a water supply pump for performing said water supply independently from said air supply pump; and
    a control section for controlling air flow and water flow rates individually by controlling said air supply pump and said water supply pump;

a second connecting pipe for connecting said water supply pump to a water channel to supply air; and an open-close valve for opening and closing said second connecting pipe, wherein said control section can supply air to said water channel by using two pumps.

3. The air and water supply system for endoscopes comprising:

an air channel for supplying air to the distal end of the endoscope;

a water channel for supplying water to said distal end of the endoscope;

an air supply pump for performing said air supply;

a water supply pump for performing said water supply independently from said air supply pump; and a control section for controlling air flow and water flow rates individually by controlling said air supply pump and said water supply pump;

a third connecting pipe for connecting said air supply pump to the water channel to supply water; and an open-close valve for opening and closing said third connecting pipe, wherein said control section supplies water to said water channel by using two pumps.

4. The air and water supply system for endoscopes according to claim 3, comprising an injection channel, apart from said water channel, for injecting water to objects under observation, said injection channel being connected to a third connecting pipe to allow water to be supplied to said injection channel with two pumps.

5. An air and water supply system for endoscopes comprising:

an air channel for supplying air to the distal end of the endoscope; a water channel for supplying water to said distal end of the endoscope;

an air supply pump for performing said air supply;

a water supply pump for performing said water supply independently from said air supply pump; and a control section for controlling air flow and water flow rates individually by controlling said air supply pump and said water supply pump;

flow control means for variably controlling the flow rate of said air or water supply through said channel;

a control switch for selecting the flow rate to be controlled by said flow control means and for performing said air supply or water supply; and a control section which controls said flow control means so as to supply air or water at a predetermined fixed flow rate for a specified time after said air supply or water supply operation is started by said control switch and then enable any flow rate specified by said control switch.

* * * * *